United States Patent
Blansett

(10) Patent No.: US 7,153,269 B1
(45) Date of Patent: Dec. 26, 2006

(54) METHOD AND SYSTEM FOR ESTIMATION OF BLOOD PRESSURE DURING CUFF INFLATION

(75) Inventor: Robert L. Blansett, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/326,022

(22) Filed: Jan. 5, 2006

(51) Int. Cl.
*A61B 5/02* (2006.01)

(52) U.S. Cl. .................. 600/490; 600/493; 600/494

(58) Field of Classification Search ............... None
See application file for complete search history.

(56) References Cited

U.S. PATENT DOCUMENTS

| | | | |
|---|---|---|---|
| 4,360,029 A | | 11/1982 | Ramsey, III |
| 4,394,034 A | | 7/1983 | Murphy et al. |
| 4,461,266 A | | 7/1984 | Hood, Jr. et al. |
| 4,543,962 A | | 10/1985 | Medero et al. |
| 4,546,775 A | | 10/1985 | Medero |
| 4,638,810 A | | 1/1987 | Ramsey, III et al. |
| 4,754,761 A | | 7/1988 | Ramsey, III et al. |
| 4,926,873 A | * | 5/1990 | Frankenreiter .............. 600/494 |
| 4,953,557 A | * | 9/1990 | Frankenreiter et al. ..... 600/493 |
| 4,985,636 A | | 1/1991 | Fukui et al. |
| 5,052,397 A | | 10/1991 | Ramsey, III et al. |
| 5,170,795 A | | 12/1992 | Ramsey, III et al. |
| 5,316,006 A | * | 5/1994 | Inage et al. ................. 600/494 |
| 5,336,665 A | * | 8/1994 | Garner-Gray et al. ...... 510/101 |
| 5,577,508 A | | 11/1996 | Medero |
| 5,590,662 A | | 1/1997 | Hersh et al. |
| 6,068,601 A | | 5/2000 | Miyazaki et al. |
| 6,475,154 B1 | * | 11/2002 | Wu et al. .................... 600/494 |

* cited by examiner

*Primary Examiner*—Robert L. Nasser
(74) *Attorney, Agent, or Firm*—Andrus, Sceales, Starke & Sawall, LLP

(57) ABSTRACT

A method of operating a blood pressure measurement system that utilizes a non-invasive blood pressure (NIBP) monitor having a blood pressure cuff. During operation of the NIBP monitor, the blood pressure cuff is initially inflated. During the initial inflation, at least one pressure transducer monitors for the presence of oscillometric pulses and creates an oscillation signal. The oscillation signal is filtered and provided to a central processor. The central processor monitors for oscillometric pulses within the filtered signal and estimates a diastolic pressure and a systolic pressure for the patient. The estimated systolic and diastolic measurements taken during the initial inflation of the blood pressure cuff are used by the central processor to set a target inflation pressure and control the deflation of the blood pressure cuff from the initial inflation pressure.

9 Claims, 6 Drawing Sheets

METHOD AND SYSTEM FOR ESTIMATION OF BLOOD PRESSURE DURING CUFF INFLATION

BACKGROUND OF THE INVENTION

The present invention relates to a method of operating an automated blood pressure measuring apparatus. More specifically, the present invention relates to a method of operating an automated non-invasive blood pressure (NIBP) monitor to estimate a patient's blood pressure during the initial cuff inflation to enhance the performance of the NIBP monitor.

Automated blood pressure monitoring has rapidly become an accepted and, in many cases, essential aspect of human treatment. Such monitors are now a conventional part of the patient environment in emergency rooms, intensive and critical care units, and in the operating theater.

The oscillometric method of measuring blood pressure involves applying an inflatable cuff around an extremity of a patient's body, such as a patient's upper arm. The cuff is inflated to a pressure above the patient's systolic pressure and then the cuff pressure is reduced either continuously or incrementally in a series of small steps. A pressure sensor measures the cuff pressure, including the pressure fluctuations resulting from the beat-to-beat pressure changes in the artery under the cuff. The data from the pressure sensor is used to compute the patient's systolic pressure, mean arterial pressure (MAP) and diastolic pressure An example of the oscillometric method of measuring blood pressure is shown and described in U.S. Pat. Nos. 4,360,029; 4,394,034; and 4,638,810, which are commonly assigned with the present invention.

During the use of a conventional NIBP monitoring system, the blood pressure cuff is placed around the arm of a patient and is inflated to a pressure that fully occludes the brachial artery to prevent blood flow. The cuff is then progressively deflated and a pressure transducer detects pressure pulses as blood begins to flow past the pressure cuff. As can be understood, the selection of the initial inflation pressure determines the amount of time and deflation required before the NIBP system begins to detect cuff oscillations and blood flow. If the initial inflation pressure is selected well above the systolic blood pressure for the patient, the NIBP system over inflates the blood pressure cuff, resulting in patient discomfort and extended measurement time. Alternatively, if the initial inflation pressure is selected below the systolic blood pressure for the patient, the blood pressure cuff must re-inflate to obtain an accurate reading. Therefore, it is desirable to estimate the patient's blood pressure to control the cuff inflation and deflation to enhance the performance of a NIBP system.

SUMMARY OF THE INVENTION

The following describes a method and apparatus for monitoring the blood pressure in a patient that uses an estimation method to improve the performance of a blood pressure monitoring. The blood pressure monitoring system includes a non-invasive blood pressure (NIBP) monitor that includes a blood pressure cuff that can be placed on the patient. The blood pressure cuff is selectively inflated and deflated by a central processor, which controls the availability of pressurized air to the cuff and the position of valves that release air from the cuff. During the deflation of the blood pressure cuff, oscillometric pulses are detected and the processor calculates the blood pressure based upon the recorded oscillometric pulses.

The NIBP monitor includes at least one pressure transducer that senses the oscillometric pulses from within the blood pressure cuff. When the cuff pressure is below a diastolic pressure for the patient, no oscillometric pulses are detected and when the cuff pressure exceeds the systolic pressure for the patient, no oscillometric pulses are detected by the pressure transducer. The NIBP monitoring system may includes either a single pressure transducer or a pair of pressure transducers located within the NIBP monitor at different distances from the air compressor required to generate the source of pressurized air supplied to the blood pressure cuff.

During the initial inflation of the blood pressure cuff, the pressure transducer generates an oscillation signal that is received by the central processor. Typically, the blood pressure cuff is inflated rapidly from approximately zero pressure to an initial inflation pressure. When the NIBP monitor begins the process of inflating the pressure cuff, the oscillation signal from the pressure transducer is received by the central processor. Conventional digital filter techniques may be used to yield the oscillometric pulses. Upon receiving the filtered signal, the central processor is able to detect oscillometric pulses present during the inflation of the blood pressure cuff.

During the inflation, when the central processor detects the beginning of the oscillometric pulses, the central processor sets an estimated diastolic pressure for the patient. Since the blood pressure cuff is being rapidly inflated, the system only estimates the diastolic pressure, which can then be used to optimize the operation of the NIBP monitor during the actual determination of the patient's blood pressure.

After the detection of the initial oscillometric pulses, the central processor continues to monitor the oscillation signal from the pressure transducer. During the rapid inflation of the blood pressure cuff from the diastolic pressure to the systolic pressure, the central processor will continue to detect oscillometric pulses. Once the pressure within the blood pressure cuff exceeds the systolic pressure, no additional oscillometric pulses will be detected. Once the oscillometric pulses terminate, the central processor estimates the systolic pressure based upon the pressure at which the pulses are no loner present in the oscillation signals.

Once the central processor determines an estimated systolic pressure, the central processor terminates the inflation of the blood pressure cuff. Typically, the termination of the inflation will occur at target inflation pressure that is slightly above the estimated systolic pressure. The target inflation pressure will be slightly above the systolic pressure for the patient such that only a few pressure steps will be required to decrease the blood pressure cuff pressure down to the systolic pressure. The selection and determination of the target inflation pressure allows the NIBP monitor to operate efficiently and reduces the amount of time required to perform a blood pressure calculation for a patient.

During the determination of the blood pressure for the patient, the NIBP monitoring system decreases pressure within the blood pressure cuff in a series of steps from the target inflation pressure to a final inflation pressure. In one embodiment of the invention, the central processor of the NIBP monitoring system intelligently varies the size of each of the pressure steps based upon the blood pressure estimates determined during the initial inflation of the blood pressure cuff. Since the blood pressure estimates provide current estimates for the systolic pressure, MAP and diastolic blood pressure, the central processor can adjust the size of the pressure steps based upon the blood pressure estimates. By varying the size of the pressure steps, the system can provide enhanced measurement resolution near the systolic, diastolic and MAP while providing larger steps to bring the blood pressure cuff inflation pressure down from the systolic pressure to the MAP and from the MAP to the diastolic pressure. Thus, the blood pressure monitoring system can more effectively determine the blood pressure and operate more quickly as compared to a standard NIBP monitoring system.

BRIEF DESCRIPTION OF THE DRAWINGS

The drawings illustrate the best mode presently contemplated of carrying out the invention. In the drawings.

DETAILED DESCRIPTION OF THE PREFERRED EMBODIMENT

Figure 1:
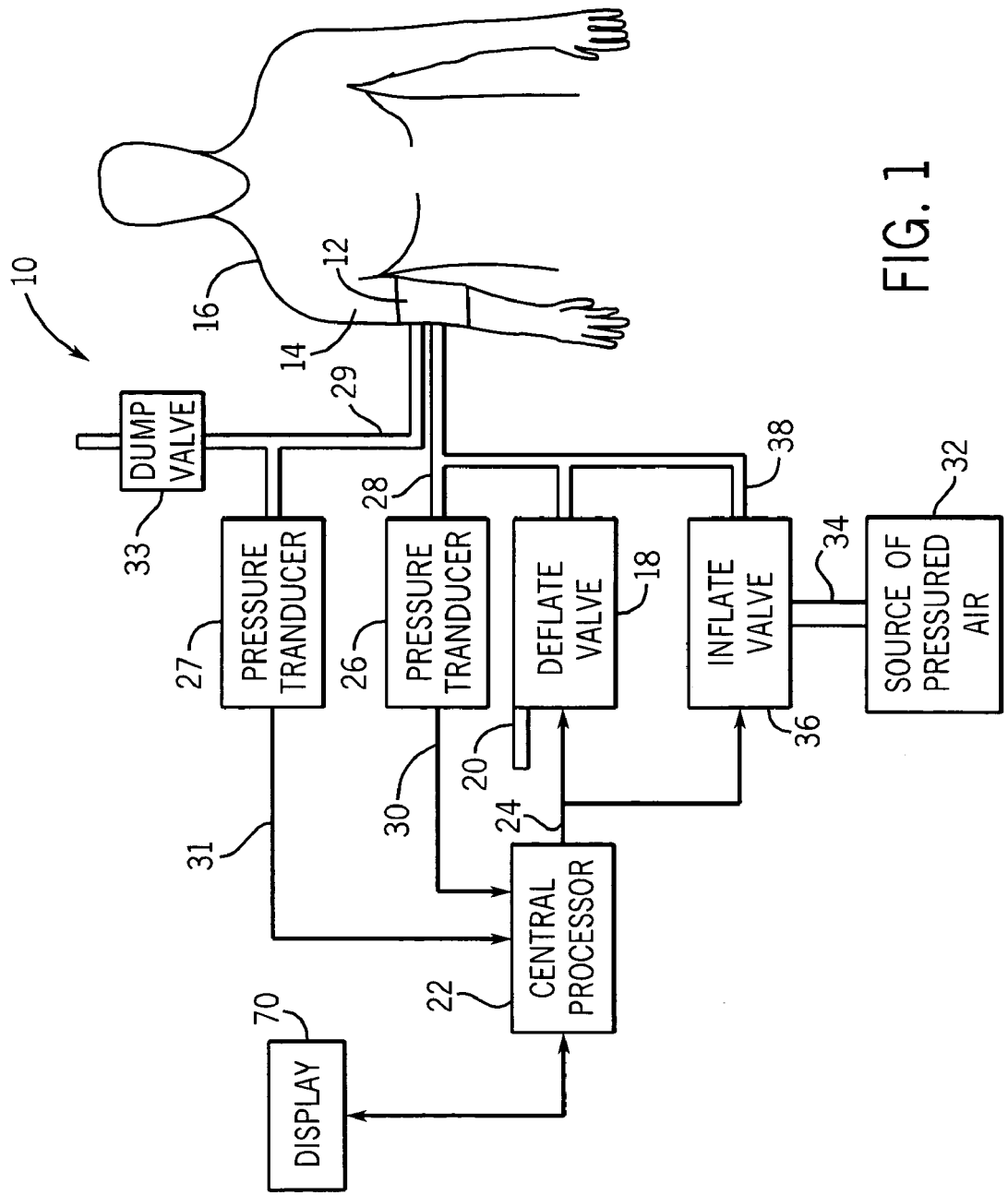
FIG. 1 is a block diagram of a system for monitoring blood pressure in a patient utilizing a NIBP monitor.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A first pressure transducer 26 is coupled by duct 28 to the blood pressure cuff 12 for sensing the pressure within the cuff 12. In accordance with conventional oscillometric techniques, the transducer 26 is used to sense pressure oscillations in the cuff 12 that are generated by pressure changes in the brachial artery under the cuff. The electrical oscillation signals from the pressure transducer 26 are obtained by the central processor 22, using an analog-to digital converter, through connection line 30.

In the embodiment of the invention illustrated, a second pressure transducer 27 is coupled by duct 29 to the blood pressure cuff 12 for sensing the pressure within the cuff 12. The duct 29 includes a dump valve 33 that can be opened to rapidly release the air pressure in the blood pressure cuff 12 to atmosphere. The electrical signals from the second pressure transducer 27 are also obtained by the central processor 22 through connection line 31. In the embodiment of the invention shown in FIG. 1, the first pressure transducer 26 and the second pressure transducer 27 are located in different areas of the NIBP monitoring system 10. The different positions of the pressure transducers 26, 27 within the NIBP monitoring system will result in different noise levels included in the oscillation signals output from the pressure transducers. For example, if one of the pressure transducers 26, 27 is located near the air compressor providing the pressurized air to the cuff, different noise levels will be present in the oscillation signal sent to the central processor 22.

A source of pressurized air 32, such as an air compressor or compressed gas cylinder, is connected by duct 34. In an embodiment incorporating an air compressor, the air compressor coupled directly to the duct 38. However, if the source of pressurized air is supplied by a compressed gas cylinder, an inflate valve 36 is positioned between the source 32 and the duct 38. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the oscillation signals from first pressure transducer 26 and/or the second pressure transducer 27 by the central processor 22 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al in U.S. Pat. No. 4,543,962, of Medero in U.S. Pat. No. 4,546,775, of Hood, Jr. et al in U.S. Pat. No. 4,461,266, of Ramsey, III et al in U.S. Pat. No. 4,638,810, of Ramsey III et al in U.S. Pat. No. 4,754,761, of Ramsey III et al in U.S. Pat. No. 5,170,795, of Ramsey III et al in U.S. Pat. No. 5,052,397, of Medero in U.S. Pat. No. 5,577,508 and of Hersh et al in U.S. Pat. No. 5,590,662, all of which are commonly assigned herewith and the disclosures of which are hereby incorporated by reference. In any event, it is desirable to use any of the known techniques to determine the quality of the oscillation complexes received at each cuff pressure so that the blood pressure determination is made using the physiological relevant cuff pressure oscillations from each heart beat and not artifacts.

Figure 2:
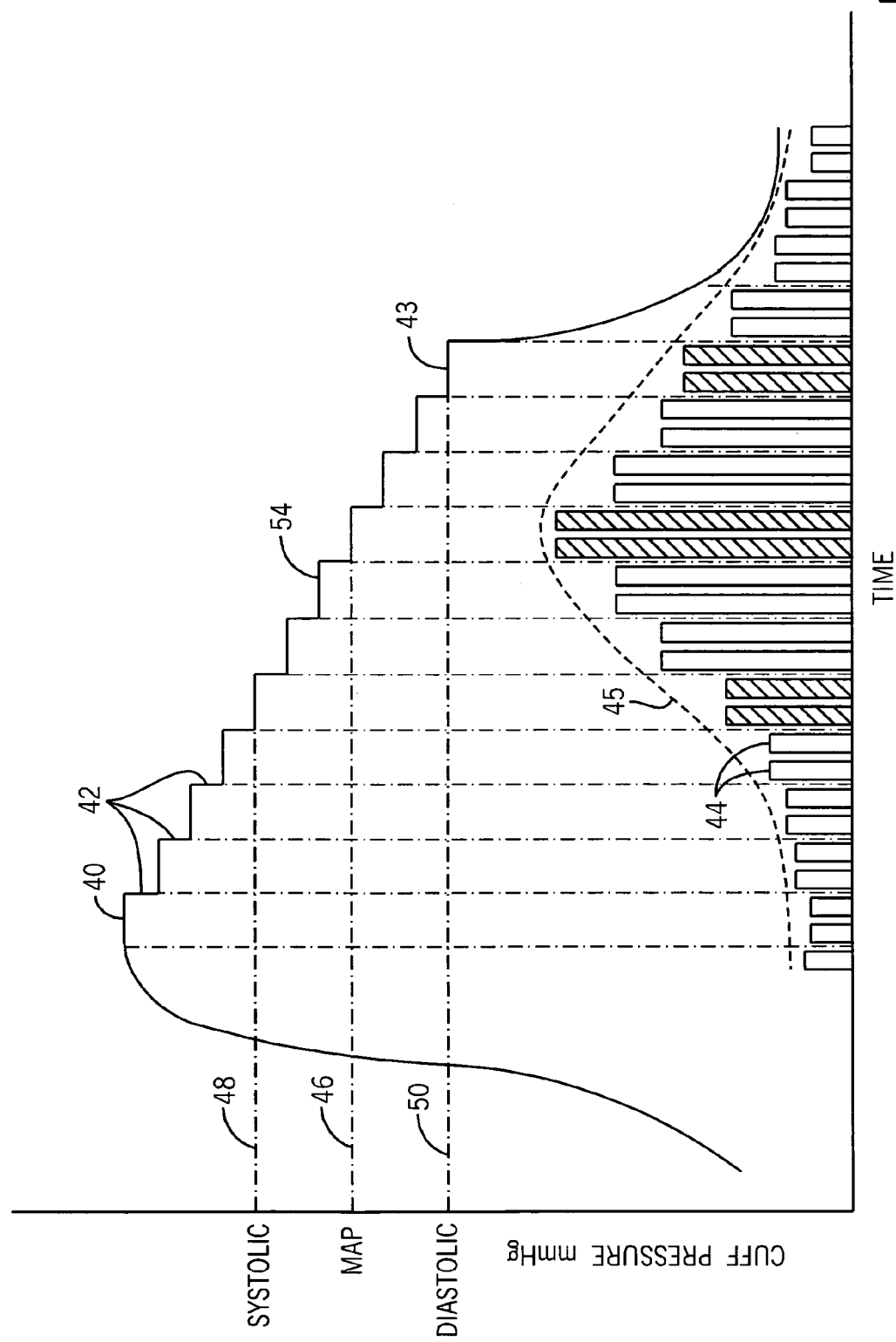
FIG. 2 is a graph depicting the over inflation of the blood pressure cuff relative to the systolic pressure, the mean arterial pressure (MAP) and diastolic pressure.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a pressure that fully occludes the brachial artery, i.e., prevents blood from flowing through the brachial artery at any point in the heart cycle. In FIG. 2, the initial inflation pressure is illustrated by reference number 40.

After the blood pressure cuff has been inflated to the initial inflation pressure 40, the deflate valve is actuated by the central processor to deflate the cuff in a series of constant pressure steps 42. Although various values for each pressure step 42 can be utilized, in one embodiment of the invention, each pressure step 42 is about 8 mm Hg per step.

After each pressure step 42, the NIBP monitoring system detects and records one or more pressure oscillations 44 for the current cuff pressure level. The pressure transducer measures the internal cuff pressure and provides an analog signal characterizing the blood pressure oscillatory complexes. The peak values of the complex signals are determined within the central processor.

Although typical cuff pressure control of the NIBP monitoring system is shown in FIG. 2 as including distinct pressure steps 42 from the initial inflation pressure 40 to a final pressure 43, the NIBP monitoring system could also operate with a continuous, smooth, or linear pressure profile from the initial inflation pressure 40 to the final pressure 43. As the cuff pressure decreases from the initial inflation pressure, the NIBP monitoring system detects pressure oscillations 44 and records the pressure oscillations for the current cuff pressure. The central processor within the NIBP monitoring system can then calculate the MAP 46, systolic pressure 48 and diastolic pressure 50.

As the measurement cycles progress, the peak amplitude of the blood pressure complexes generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by the central processor to calculate the mean arterial pressure (MAP) 46, the systolic pressure 48 and the diastolic pressure 50 in a known manner.

As can be understood in the graph of FIG. 2, the initial inflation pressure 40 for the blood pressure cuff must exceed the systolic pressure 48 of the patient for the system and method of the NIBP monitoring to function effectively. In past embodiments of the NIBP monitoring systems, the initial inflation pressure 40 is either based upon the systolic pressure 48 determined during the last measurement cycle or is set at a constant value for each patient. The systolic pressure 48 from the last measurement cycle is typically increased by a set value or percentage to determine the initial inflation pressure 40 for the next measurement cycle. Since the last blood pressure cuff measurement may have been taken at a significant time period before the current measurement, the estimated initial inflation pressure based upon the last measurement may be inaccurate due to changing conditions relative to the patient. Further, if a standard value is used for the patient, the initial pressure 40 may be much too high or even to low, depending upon the patient. In the case of the initial (or only) blood pressure measurement for the patient, there is no prior measurement from which to derive an estimate of the initial inflation pressure. In such case, the prior art system relies upon a standard value, which is the same for every patient.

In the graph of FIG. 2, the initial inflation pressure 52 is selected significantly higher than the systolic pressure 48. In this operating example, the pressure within the blood pressure cuff must be decreased a significant number of pressure steps 42 before the cuff pressure 54 reaches the systolic pressure 48. The over inflation of the blood pressure cuff results in the patient experiencing discomfort due to unnecessarily high cuff pressures and prolonged occlusion of the brachial artery. Further, the over inflation of the blood pressure cuff increases the overall time required to take a blood pressure reading from the patient due to the numerous pressure steps 42 required before the cuff pressure 54 reaches the systolic pressure 48.

In addition to the over inflation, the initial inflation pressure can be incorrectly selected to be below the systolic pressure 48. If the initial inflation pressure is below the systolic pressure 48, the NIBP monitoring system will not obtain the required oscillometric pressure measurements needed to accurately calculate the systolic pressure 48. In this situation, the NIBP monitoring system must re-inflate the blood pressure cuff to an inflation pressure that is greater than the systolic pressure 48. In such a situation, the patient again experiences unnecessary reinflation of the cuff, which prolongs the blood pressure determination time and increases patient discomfort.

Although the method of estimating the initial inflation pressure from earlier blood pressure determinations is generally effective, the initial inflation pressure may be in error if the patient's blood pressure has changed significantly in the time between the current NIBP measurement and the previous NIBP determination. In some cases, the amount of time between blood pressure measurements may be 15 minutes to an hour. If the patient's blood pressure has changed significantly in that time period, the standard inflation adjustment may be incorrect and result in either over inflation or under inflation, thereby prolonging the blood pressure determination cycle.

Figure 3:
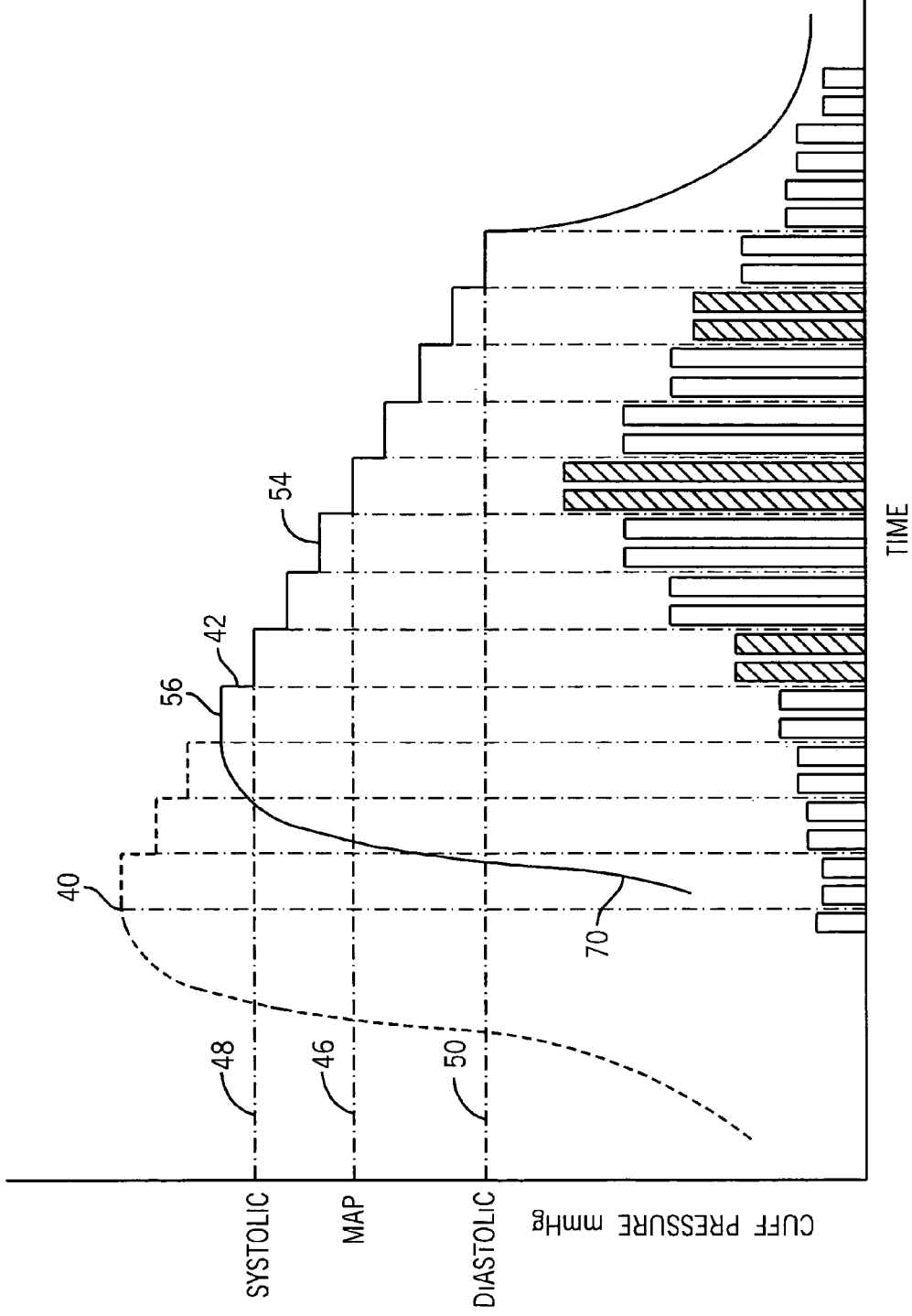
FIG. 3 is a graph illustrating the optimized inflation of the blood pressure cuff to a target inflation pressure based upon estimates made during inflation.

Referring now to FIG. 3, it is desirable for the blood pressure cuff of the NIBP monitoring system to be inflated to target inflation pressure 56 that is only slightly above the systolic pressure 48 for the patient. As illustrated in FIG. 3, the target inflation pressure 56 is only a single pressure step 42 above the systolic pressure 48. In the conventional NIBP monitor, the initial inflation pressure 40 is well above the systolic pressure 48 such that a series of pressure steps are required to drop the cuff pressure 54 to the systolic pressure 48, as illustrated by the broken lines in FIG. 3. The determination of the target inflation pressure 56 will be shown and described with reference to FIG. 5.

Figure 5:
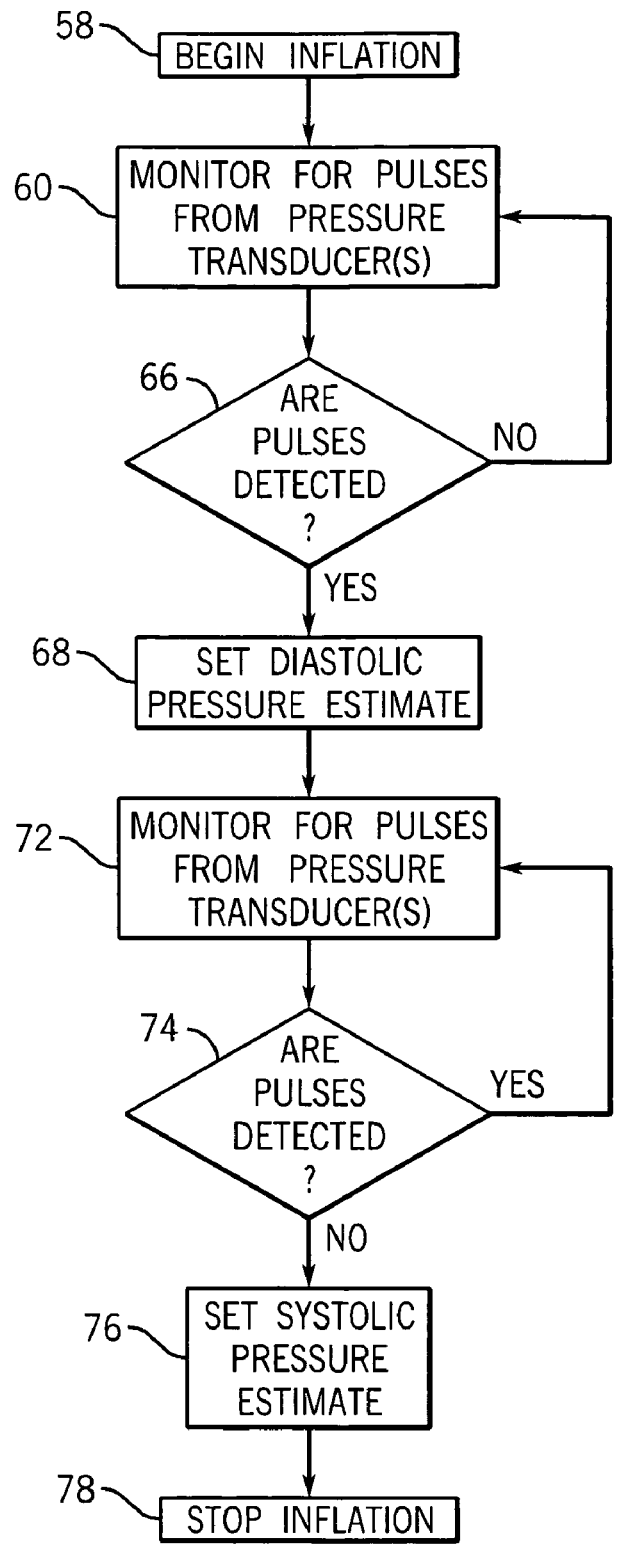
FIG. 5 is a flow chart illustrating the operation of a central processor in estimating the systolic and diastolic pressure and controlling the inflation of the blood pressure cuff.

As indicated in FIG. 5, the central processor begins the initial inflation of the blood pressure cuff as shown in step 58. As the blood pressure cuff is inflated, a central processor 22 receives a first oscillation signal from the first pressure transducer 26 and a second oscillation signal from the second pressure transducer 27, as best shown in FIG. 1. As illustrated in FIG. 5, the central processor monitors for the presence of oscillometric pulses in the first and second oscillation signals from the first and second pressure transducers in step 60. In the embodiment of the invention illustrated, the NIBP monitoring system includes both the first and second pressure transducers 26, 27. However, it should be understood that it is possible to utilize only a single pressure transducer while operating within the scope of the present invention.

Figure 6:
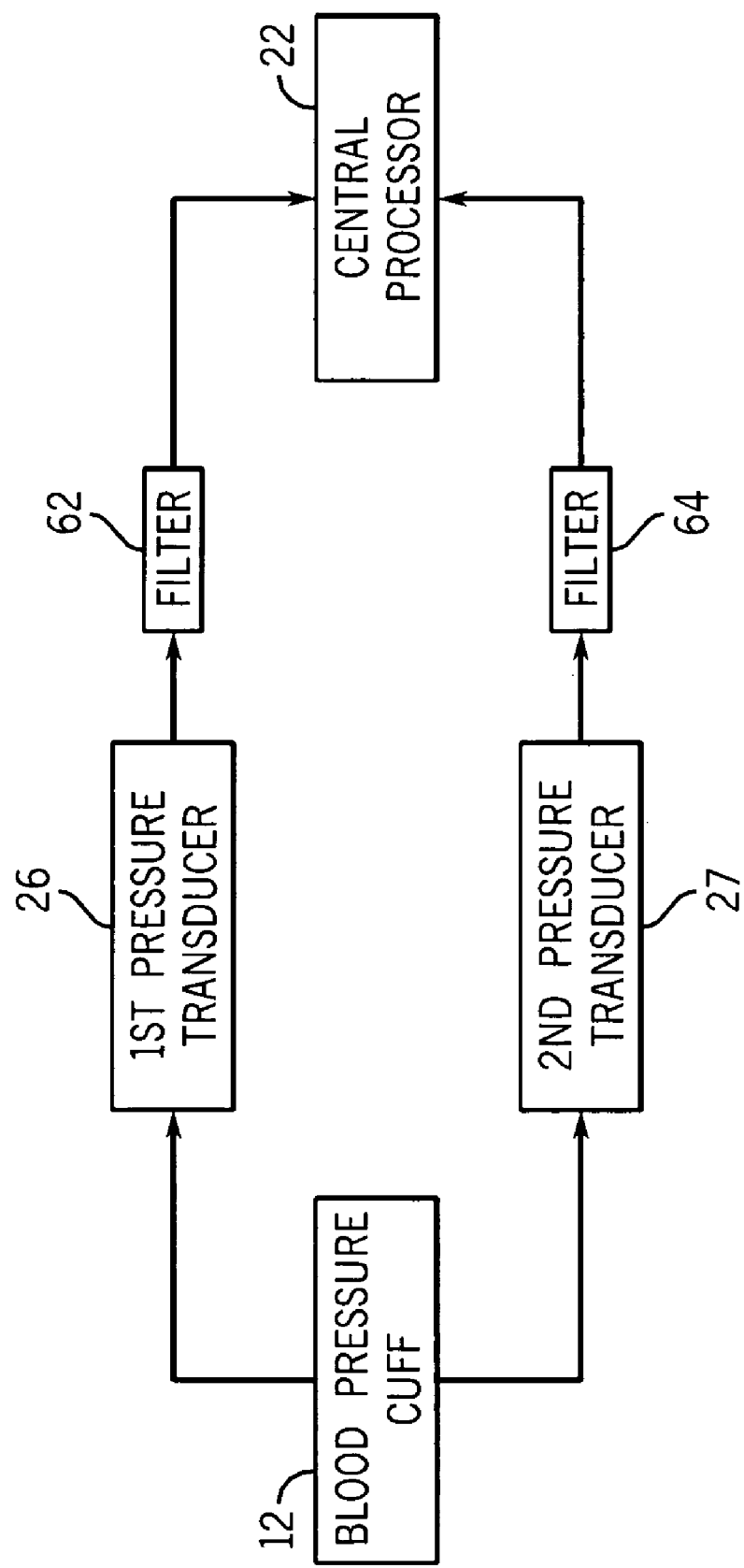
FIG. 6 is a schematic illustration of the filtering of the oscillation signals from the first and second pressure transducers.

In the embodiment of the invention shown in FIG. 1, the oscillation signals from the first and second pressure transducers 26, 27 are transferred directly to the central processor 22 through the respective connection lines 30, 31. However, it is contemplated that the oscillation signals from the first and second transducers 26, 27 could each be fed through a digital filter 62, 64 prior to the signal being received at the central processor 22, as shown in FIG. 6. During the initial inflation of the blood pressure cuff, the oscillation signals from the first and second transducers 26, 28 include a significant amount of noise, typically introduced by the operation of the air compressor supplying the source of pressurized air to the blood pressure cuff. The filters 62, 64 can be selected to remove a significant amount of the noise included within each of the oscillation signals from the first and second pressure transducers 26, 27. As an example, when an air compressor is used to inflate the blood pressure cuff, the blood pressure frequency components will be primarily less than 30 Hz, while the compressor frequency components will be primarily above 30 Hz. In this configuration, each of the filters 62, 64 will be low-pass filters having a cutoff frequency of approximately 30 Hz to remove the compressor oscillation with minimal impact on the blood pressure wave form. It is contemplated that the filters 62, 64 could be digital filters that are selected to remove the noise levels typically associated with the operation of the air compressor used to create the pressurized air to inflate the blood pressure cuff.

As illustrated in FIG. 6, the filtered oscillation signals from both the first pressure transducer 26 and the second pressure transducer 27 are supplied to the central processor 22. Upon receiving the filtered oscillation signals, the central processor can select the filtered oscillation signal that includes the least amount of noise. Alternatively, the central processor can combine the two filtered oscillation signals and average the results to extract the oscillometric pulses. The operation of the central processor 22 and the selection of the pair of filters 62, 64 can be varied depending upon the noise introduced into the oscillation signals by the air compressor, as can be understood by those skilled in the art. In an embodiment that includes only a single pressure transducer, the oscillation signal from the single pressure transducer will be digitally filtered and received by the central processor. In either case, the central processor can monitor for oscillometric pulses in the filtered oscillation signal from either a single pressure transducer or a pair of pressure transducers.

Figure 4:
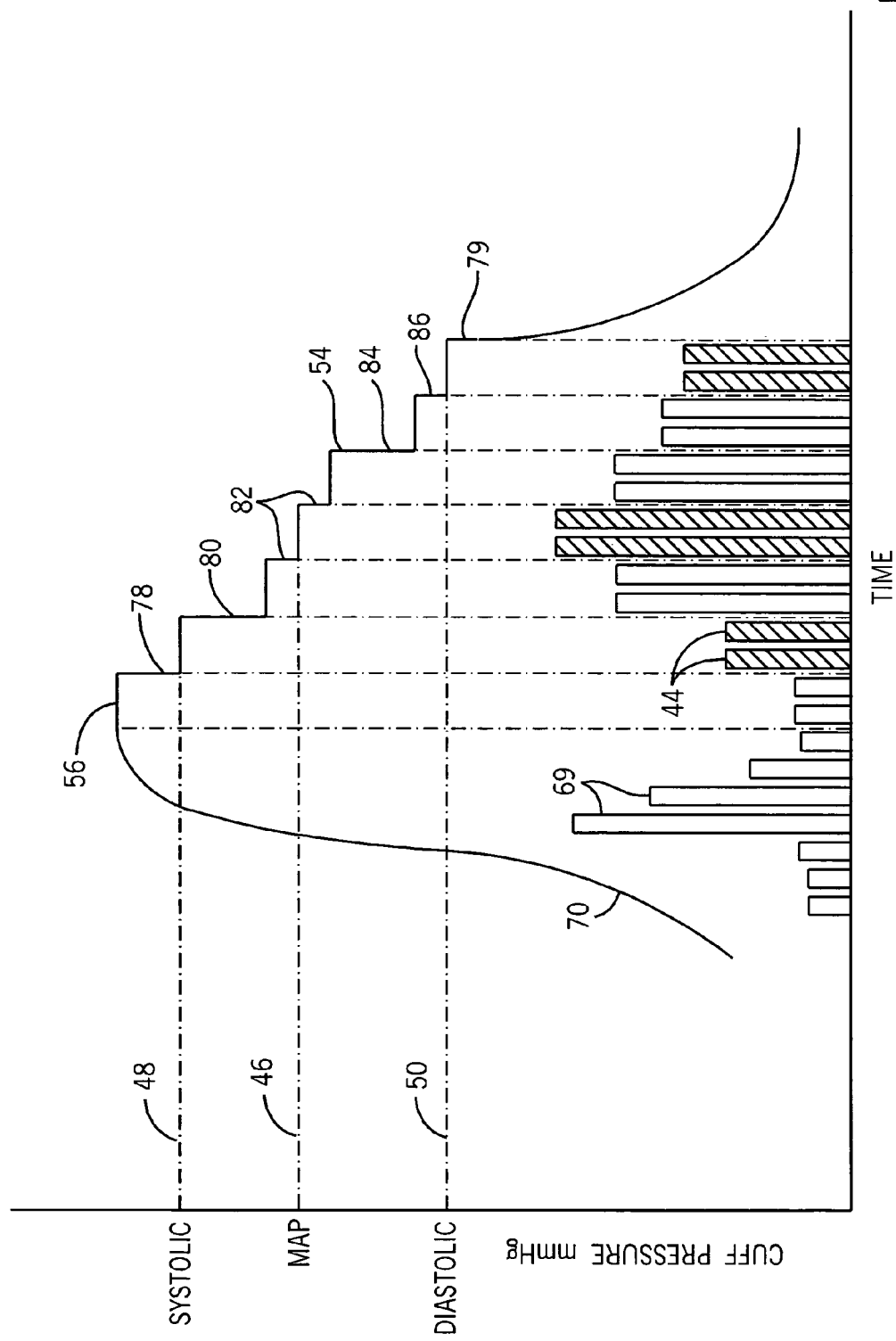
FIG. 4 is a graph illustrating the variable step heights from the target inflation pressure to a final pressure below the diastolic pressure as well as the oscillometric pulses detected during inflation.

The filtered oscillation signal from either one or both of the filters 62, 64 during the initial inflation will include a series of oscillometric pulses, as illustrated by the pulses 69 positioned beneath the inflation curve 70 of FIG. 4. Each of the oscillometric pulses 69 detected during the initial inflation period 71 generally correspond in intensity to the pulses 44 detected during the deflation of the blood pressure cuff from the target inflation pressure 56 for the same cuff pressure levels. The pulses 69 detected during the inflation period 71 can be interpreted by the central processor to estimate at least the systolic pressure and determine the target inflation pressure 56. Since the inflation period 71 is much shorter than the deflation period from the target inflation pressure 56 to the final pressure 79, the oscillometric pulses detected during the inflation period 71 are insufficient to calculate a final blood pressure for the patient. However, the oscillometric pulses 69 detected during the inflation period 71 can be utilized to optimize the operation of the blood pressure monitoring device.

Referring back to FIG. 5, the central processor 22 determines whether any pulses are present in the filtered oscillation signal in step 66. If the central processor determines that no oscillometric pulses are present, the central processor returns to step 60 and continues to monitor for oscillometric pulses within the oscillation signal from the pressure transducer.

During the inflation of the blood pressure cuff, only very small, if any, oscillometric pulses will be detected within the oscillation signal from the first or second pressure transducer 26, 27 until the cuff pressure reaches the diastolic pressure 50, as best shown in FIG. 4.

Once the central processor detects the presence of oscillometric pulses in step 66, the central processor will set an estimated diastolic pressure at the instantaneous cuff pressure when the first oscillometric pulse was detected, as shown in step 68. Since the blood pressure cuff is inflated very quickly, as illustrated by the steep portion of inflation curve represented by reference numeral 70 in FIG. 4, the diastolic pressure determined during the initial inflation is a very rough estimate and is not accurate enough to represent the diastolic pressure for the patient. However, during the initial inflation of the blood pressure cuff, the central processor can estimate the diastolic pressure based upon the cuff pressure when the first oscillometric pulse is detected.

Referring back to FIG. 5, after the first oscillometric pulses are detected, the central processor continues to monitor for pulses from the pressure transducer, as illustrated in step 72. If pulses continue to be detected in step 74, the control unit continues to inflate the blood pressure cuff and monitor for the presence of oscillometric pulses. Oscillometric pulses will be present within the oscillation signal from the pressure transducer until the cuff pressure reaches the systolic pressure 48 for the patient. Once the cuff pressure reaches the systolic pressure, oscillometric pulses will no longer be detected. Once pulses are no longer present in the oscillation signal, the central processor will set an estimated systolic pressure to be the instantaneous cuff pressure when the oscillometric pulses are no longer present, as illustrated by step 76. Once the systolic pressure estimate is determined in step 76, the central processor will terminate the inflation of the blood pressure cuff, as shown in step 77.

In a preferred embodiment of the invention, the central processor will stop inflating the blood pressure cuff at the target inflation pressure 56 shown in FIG. 3. Since the central processor can generate only a very rough estimate for the systolic pressure during the rapid inflation shown by inflation curve 70, the target inflation pressure is determined by the estimated systolic pressure plus a predetermined offset amount. The predetermined offset amount ensures that the target inflation pressure 56 is above the systolic pressure 48 such that reinflation of the blood pressure cuff will not be required due to an underinflation of the pressure cuff below the systolic pressure. As illustrated in FIG. 3, the target inflation pressure 56 more closely corresponds to the actual systolic pressure 48 as compared to the initial inflation pressure 40 calculated by using a conventional NIBP monitoring system alone.

Referring now to FIG. 4, in addition to utilizing the estimated systolic pressure calculated during the inflation of the blood pressure cuff to set a target inflation pressure, the central processor can also utilize the estimated blood pressure measurements to adjust the size of the pressure steps from the target inflation pressure 56 down to the final pressure 79. As illustrated in FIG. 4, the central processor operates the deflate valve to create a first pressure step 78 to step the cuff pressure down from the target inflation pressure 56. As an example, the first pressure step 78 may have the typical value of 8 mm Hg similar to the system shown in FIG. 2. The first pressure step 78 steps the cuff pressure 54 to a value close to the systolic pressure 48, as determined by the estimate calculated during the initial inflation of the blood pressure cuff. After the oscillations 44 have been measured, the central processor generates a second pressure step, step 80, to step the cuff pressure 54 down to near the MAP 46, as was also estimated by the central processor based upon the estimated systolic and diastolic pressures.

Once the cuff pressure 54 nears the MAP, the central processor creates a series of smaller steps 82 having pressure decrements much smaller than the first pressure step 78 and the second pressure step 80. As an example, the smaller pressure steps 82 could be only 6 mm Hg. It should be understood that in the above description, the values given for the first and second pressure steps 78,80 and the smaller steps 82 are for illustrative purposes and that the values can be varied depending upon the patient and the pressure control capabilities of the NIBP system. The smaller size of the series of the steps 82 allows the system to have increased resolution that pressures near the MAP 46.

Once the central processor detects the rise of the pressure oscillations 44 and the subsequent fall following the MAP 46, the central processor again increases the size of the pressure steps, as indicated by the third pressure step 84. Although only a single third pressure step 84 is shown in FIG. 4, it should be understood that the size of the pressure step 84 could vary and that multiple steps could be required between the MAP 46 and the diastolic pressure 50.

Once the cuff pressure 54 approaches the diastolic pressure 50, a second series of smaller steps 86 are created by the central processor. Once again, at a pressure location near the diastolic pressure 50, the system provides for additional pressure steps to more accurately determine the diastolic pressure 50.

As can be understood by the description of FIG. 4, the central processor can use the estimated systolic and diastolic blood pressure measurements determined during the initial inflation of the blood pressure cuff to set the optimized target inflation pressure 56 and vary the pressure step sizes from the target inflation pressure 56 down to the final pressure 79. In this manner, the system can provide for enhanced measurements near the systolic, MAP and diastolic pressures while increasing the step sizes to allow the cuff pressure 54 to fall more quickly at locations between the systolic pressure and the MAP, as well as the MAP and the diastolic pressure. A similar methodology could be applied to a monitor using linear deflation by varying the rate of deflation so that an increase in the deflation rate corresponds to a larger step.

Various alternatives and embodiments are contemplated as being within the scope of the following claims particularly pointing out and distinctly claiming the subject matter regarded as the invention.

What is claimed is:

1. A method of monitoring blood pressure in a patient, the method comprising the steps of:
   providing a non-invasive blood pressure (NIBP) monitor having a selectively inflatable and deflatable blood pressure cuff, a first pressure transducer and a second pressure transducer for detecting oscillometric pulses;
   inflating the blood pressure cuff;
   monitoring for the presence of oscillometric pulses from the first and second pressure transducers during the inflation of the blood pressure cuff;
   receiving a first oscillation signal from the first pressure transducer and a second oscillation signal from the second pressure transducer during the inflation of the blood pressure cuff;
   filtering the first and second oscillation signals to remove noise and extract the oscillometric pulses;
   selecting either the first filtered oscillation signal or the second filtered oscillation signal based upon which filtered oscillation signal includes the least amount of noise;
   estimating at least the systolic blood pressure and the diastolic blood pressure for the patient based upon the oscillometric pulses contained in the selected first or second filtered oscillation signal;
   terminating the inflation of the blood pressure cuff at a target inflation pressure above the estimated systolic blood pressure;
   deflating the blood pressure cuff from the initial inflation pressure;
   monitoring for oscillometric pulses from one of the first or second pressure transducers during the deflation of the blood pressure cuff from the target inflation pressure; and
   determining at least the systolic pressure, mean arterial pressure and diastolic pressure of the patient based upon the oscillometric pulses detected during the deflation of the blood pressure cuff from the target inflation pressure.

2. The method of claim 1 further comprising the step of estimating the diastolic blood pressure for the patient based upon the oscillometric pulses contained in the selected first and second filtered oscillation signal.

3. The method of claim 2 further comprising the steps of:
   deflating the blood pressure cuff in a series of pressure steps from the target inflation pressure;
   monitoring for the presence of oscillometric pulses from one of the first or second pressure transducer during the deflation of the blood pressure cuff from the target inflation pressure; and
   determining the systolic pressure, mean arterial pressure and diastolic pressure for the patient based upon the oscillometric pulses detected during the deflation of the blood pressure cuff from the target inflation pressure.

4. The method of claim 3 further comprising the step of varying the size of the pressure steps based upon the estimated blood pressure determined during inflation of the blood pressure cuff.

5. The method of claim 1 wherein the first pressure transducer and the second pressure transducer are located remotely from each other.

6. The method of claim 1 wherein the inflation of the blood pressure cuff is terminated a predetermined amount above the estimated systolic pressure.

7. The method of claim 1 further comprising the steps of:
   deflating the blood pressure cuff in a series of pressure steps from the target inflation pressure; and
   varying the size of the pressure steps during the deflation of the blood pressure cuff based upon the estimated systolic blood pressure and the estimated diastolic blood pressure.

8. A method of monitoring blood pressure in a patient, the method comprising the steps of:
   providing a non-invasive blood pressure (NIBP) monitor having a selectively inflatable and deflatable blood pressure cuff, a first pressure transducer and a second pressure transducer each for detecting oscillometric pulses from the patient;
   inflating the blood pressure cuff;
   monitoring for the presence of oscillometric pulses from both the first pressure transducer and the second pressure transducer during the inflation of the blood pressure cuff;
   receiving a first oscillation signal from the first pressure transducer and a second oscillation signal from the second pressure transducer during the inflation of the blood pressure cuff;
   filtering the first and second oscillation signals to extract the oscillometric pulses;
   selecting either the first filtered oscillation signal or the second filtered oscillation signal based upon which filtered oscillation signal includes the least amount of noise;
   estimating at least the systolic blood pressure for the patient based on the oscillometric pulses contained in the selected first or second filtered oscillation signal; and
   terminating the inflation of the blood pressure cuff at a target inflation pressure above the estimated systolic blood pressure.

9. The method of claim 1 wherein the inflation of the blood pressure cuff is terminated a predetermined amount above the estimated systolic pressure.

* * * * *